United States Patent [19]
Bird

[11] Patent Number: 4,805,613
[45] Date of Patent: Feb. 21, 1989

[54] VENTILATOR WHICH CAN BE READILY TRANSPORTED FOR EMERGENCY SITUATIONS

[76] Inventor: Forrest M. Bird, P.O. Box 817, Sandpoint, Id. 93964

[21] Appl. No.: 866,791

[22] Filed: May 23, 1986

[51] Int. Cl.$^4$ ........................................... A61M 16/00
[52] U.S. Cl. ........................ 128/204.25; 128/205.24; 137/102; 417/183
[58] Field of Search ......... 128/204.18, 204.26–204.27, 128/205.21, 205.24, 205.26, 204.28, 205.11; 137/102, 888; 417/183–185

[56] References Cited

U.S. PATENT DOCUMENTS

| | | | |
|---|---|---|---|
| 4,243,155 | 1/1981 | Stewart | 128/204.18 X |
| 4,437,461 | 3/1984 | Greenberg | 128/205.24 |
| 4,502,481 | 3/1985 | Christian | 128/205.24 |
| 4,592,349 | 6/1986 | Bird | 128/205.24 X |
| 4,624,251 | 11/1986 | Miller | 128/205.24 X |

Primary Examiner—Kyle L. Howell
Assistant Examiner—Angela D. Sykes
Attorney, Agent, or Firm—Flehr, Hohbach, Test, Albritton & Herbert

[57] ABSTRACT

Ventilator adapted to be connected to a source of gas under pressure comprising a case and an inlet adapted to be connected to the source of gas. It also is comprised of an oscillator cartridge carried by the case and having a body with an inlet and an outlet and a flow passage interconnecting the inlet and the outlet. A valve member is carried by the body and is movable between open and closed positions with respect to the outlet. A diaphragm is carried by the body and is connected to the valve member for moving the valve member between and open and closed positions to interrupt the flow of gas in the flow passage between the inlet and the outlet. A servo port is carried by the body for supplying gas to the diaphragm for causing movement of the diaphragm to thereby cause movement of the valve member to the closed position to interrupt the flow of gas in the flow passage between the inlet and the outlet. An adjustable metering valve meters the flow of gas from the outlet to the servo port to provide for cyclic operation of the oscillation cartridge between inspiratory and expiratory phases. A patient adapter having an inlet and an outlet and a pneumatic clutching device having an inlet and an outlet is coupled to the inlet of the patient adapter. The outlet of the oscillator cartridge is coupled to the inlet of the pneumatic clutching device. The adjustable metering valve has a single control knob which changes the frequency of cyclic operation and the ratio between the inspiratory phase and the expiratory phase.

14 Claims, 7 Drawing Sheets

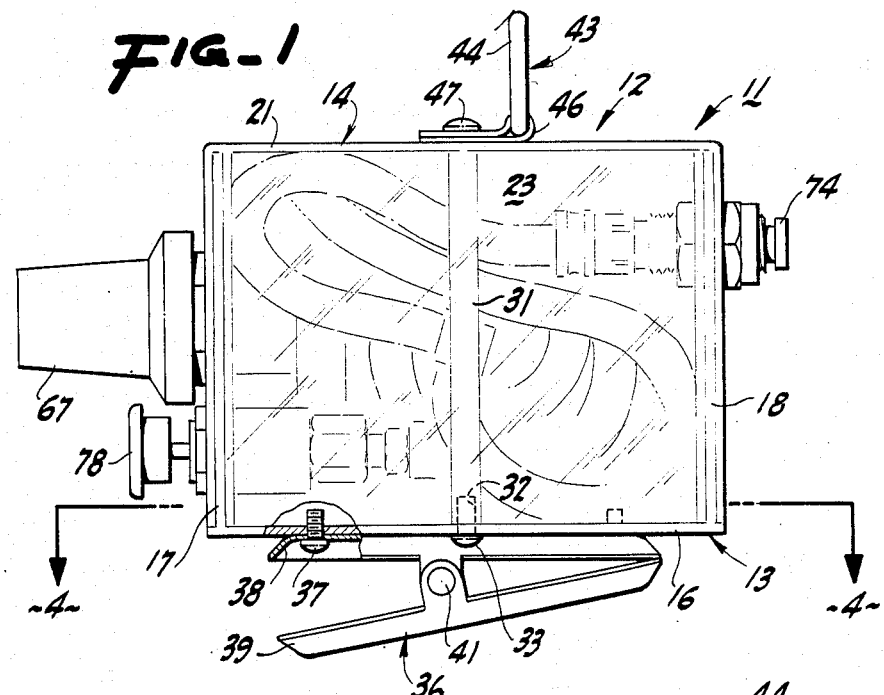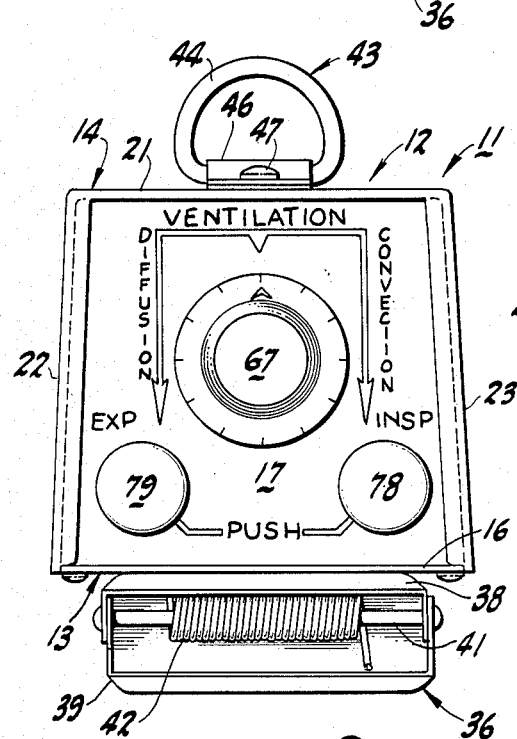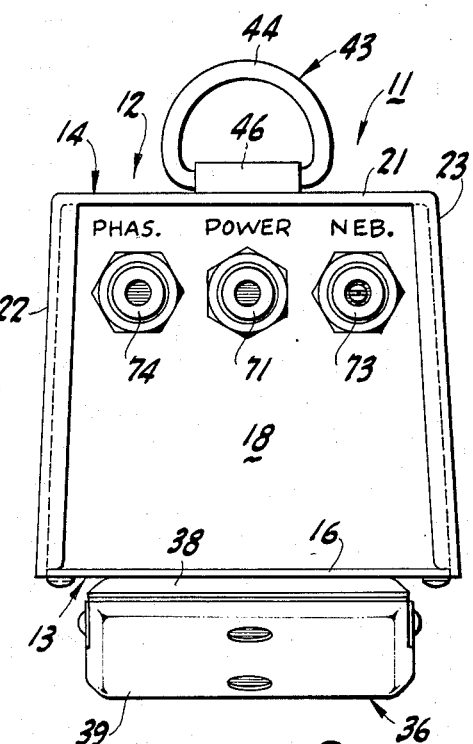

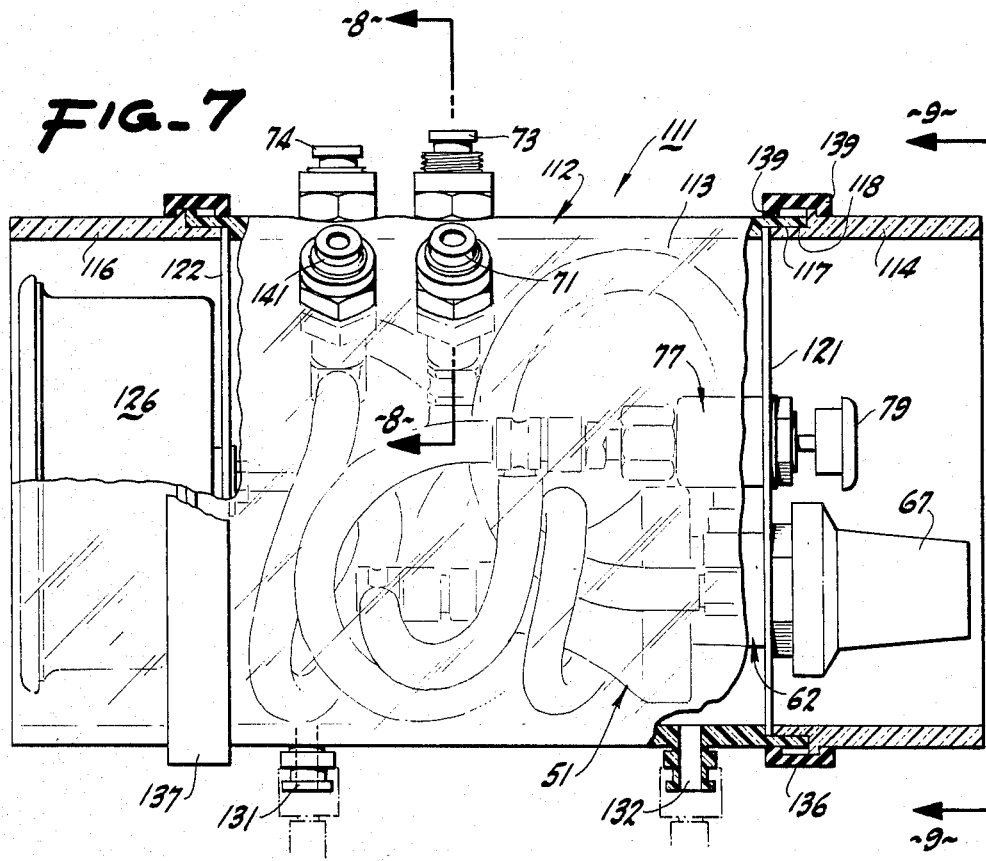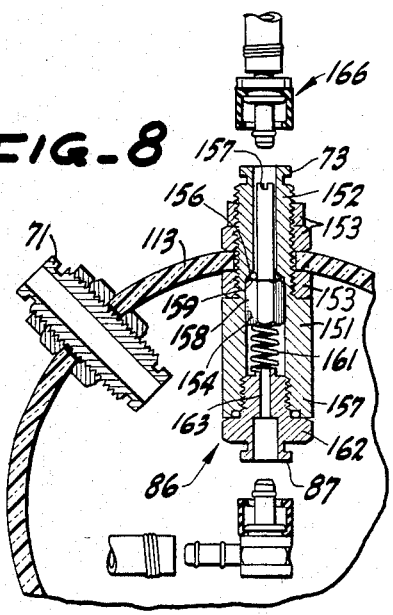

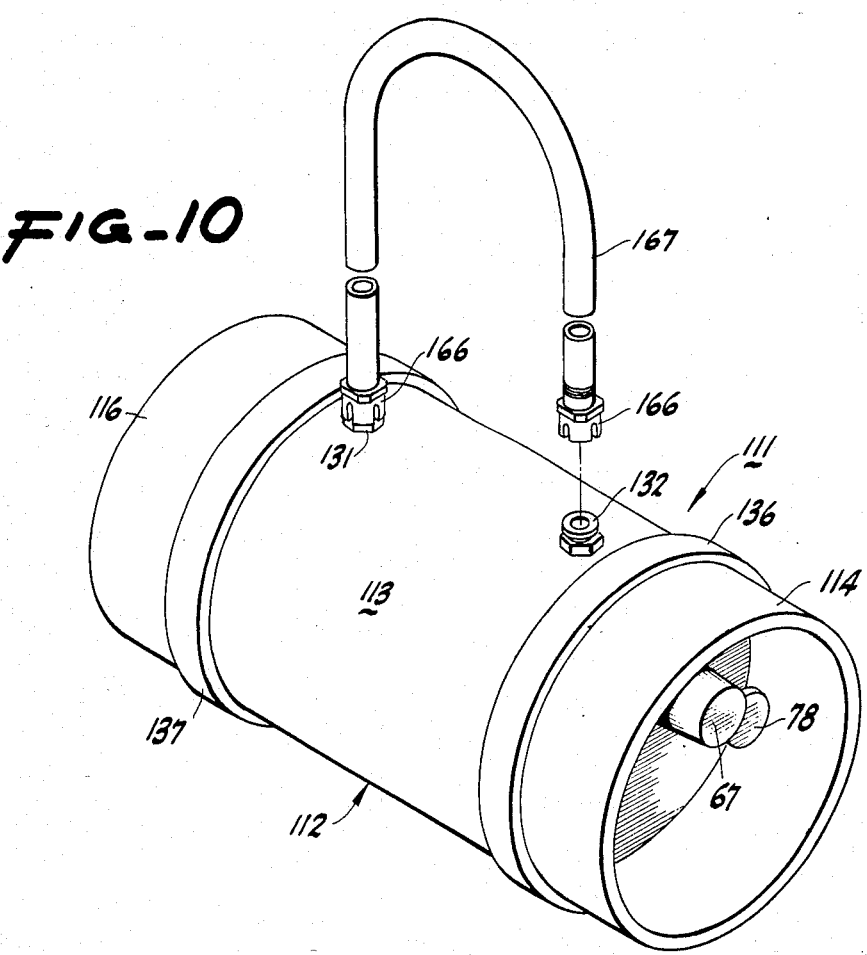
FIG-10
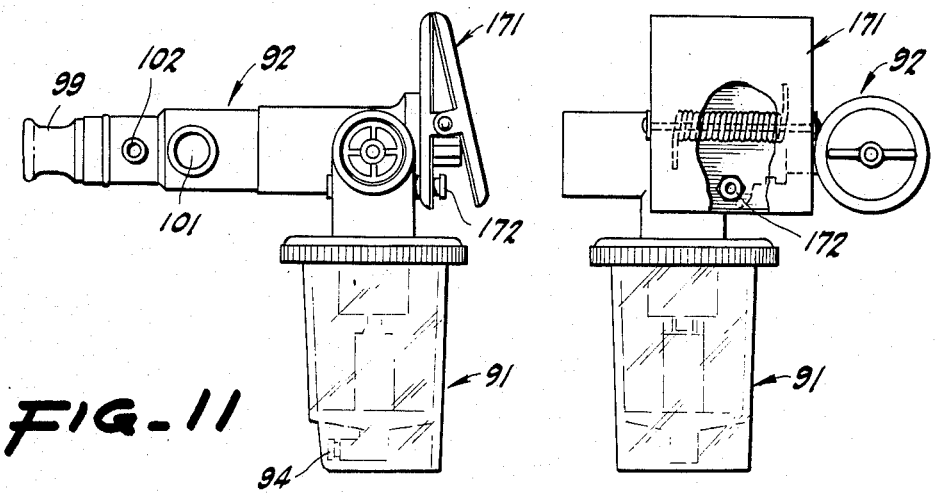
FIG-11
FIG-12

VENTILATOR WHICH CAN BE READILY TRANSPORTED FOR EMERGENCY SITUATIONS

SUMMARY OF THE INVENTION

This invention relates to a ventilator and, more particularly, to a ventilator which can be readily transported for emergency situations.

Ventilators heretofore have been provided. For example, ventilators of the type described in co-pending application Ser. No. 671,491 filed on Nov. 14, 1984 have been provided. However, such ventilators are relatively complex and do not lend themselves to transportability for emergency applications. There is therefore a need for a new and improved ventilator.

In general, it is an object of the present invention to provide a ventilator which can be readily transported from one location to another.

Another object of the invention is to provide a ventilator of the above character which is very simple and can be utilized for transporting patients from a site of trauma to a formal hospital facility.

Another object of the invention is to provide a ventilator of the above character which is very light in weight.

Another object of the invention is to provide a ventilator of the above character which can be operated by relatively unskilled personnel.

Another object of the invention is to provide a ventilator of the above character which is economical in its use of gas.

Another object of the invention is to provide a ventilator of the above character which is relatively small and compact.

Another object of the invention is to provide a ventilator of the above character which has military applications.

Another object of the invention is to provide a ventilator of the above character which can be used in the event of biological warfare.

BRIEF DESCRIPTION OF THE DRAWINGS

Additional objects and features of the invention will appear from the following description in which the preferred embodiments are set forth in detail in conjunction with the accompanying drawings.

FIG. 1 is a side elevational view of a ventilator incorporating the present invention.

FIG. 2 is a front elevational view of a ventilator shown in FIG. 1.

FIG. 3 is a rear elevational view of the ventilator shown in FIG. 1.

FIG. 7 is a side elevational view of another embodiment of a ventilator incorporating the present invention.

FIG. 8 is a partial cross-sectional view taken along the line 8—8 of FIG. 7.

FIG. 9 is an end elevational view looking along the line 9—9 of FIG. 7.

FIG. 10 is an isometric view of the ventilator shown in FIG. 7 showing the use of a carrying strap.

FIG. 11 is a side elevational view of the nebulizer and a combination venturi and exhalation valve assembly.

FIG. 12 is a side elevational view taken at right angles to the view shown in FIG. 11.

DESCRIPTION OF THE PREFERRED EMBODIMENTS

Figure 4:
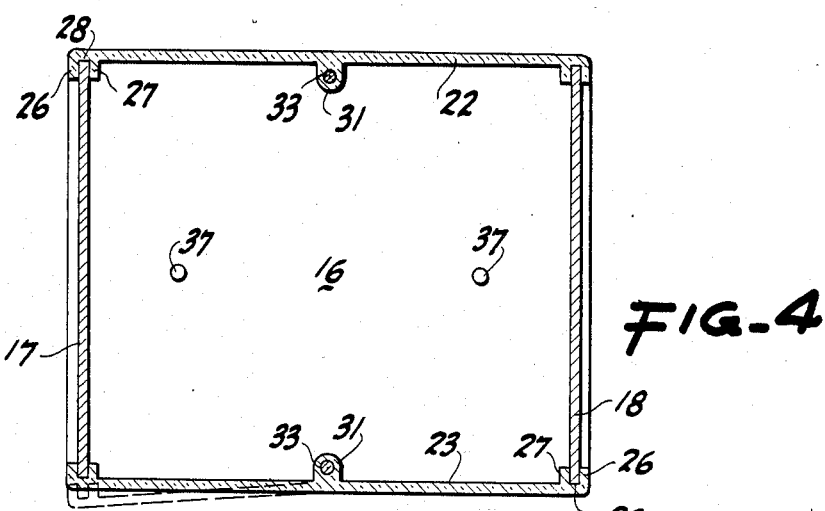
FIG. 4 is a cross sectional view taken along the line 4—4 of FIG. 1.

In general the ventilator of the present invention is adapted to be connected to a source of gas under pressure. It consists of a case and an inlet adapted to be connected to the source of gas. It also consists of an oscillator cartridge which is carried by the case and having a body. The body has an inlet and an outlet and a flow passage interconnecting the inlet and the outlet. A valve member is carried by the body and is movable between open and closed positions with respect to the outlet carried by the body. A diaphragm is carried by the body and connected to the valve member. A servo port is carried by the body and is used for supplying gas to one side of the diaphragm for causing movement of the diaphragm to thereby cause the valve member to move to a closed position to occlude the flow of gas from the inlet to the outlet. An adjustable metering valve is provided for metering the flow of gas to the servo port. A patient adapter is provided. Pneumatic clutching means having an input and having output. The output is coupled to the patient adapter. Means is provided for coupling the output of the oscillator cartridge body to the input of the pneumatic clutching means. Explosive decompression means is carried by the case.

More, in particular ventilator 11 which is shown in FIGS. 1-5 of the drawing includes a case 12 which is very similar to the case disclosed in co-pending application Ser. No. 866,790 filed May 23, 1986, now abandoned in favor of Ser. No. 111,139, filed Oct. 19, 1987. More in particular, the ventilator shown in FIGS. 1, 2, 3, 4 and 5 of the drawings consists of a case 12.

The case 12 is formed of two U-shaped parts, 13 and 14. The two U-shaped parts 13 and 14 can be formed with suitable material such as plastic. By way of example, the part 13 can be opaque whereas the part 14 can be formed of a transparent plastic. The U-shaped part 13 is provided with a bottom wall 16 and front and rear walls 17 and 18 which extend at substantially right angles to the bottom wall 16. Similarly, the U-shaped part 14 is provided with a top wall 21 and side walls 22 and 23 which extend at substantially right angles to the top wall 21. Each of the side walls 22 and 23 is provided with a pair of ribs 26 and 27 (see FIG. 4) at each end of the side wall and extending longitudinally of the side wall to provide a slot 28 therebetween extending longitudinally thereof. In addition, a rib 31 is formed integral with each of the side walls 22 and 23. The lower extremities of the ribs 31 are provided with holes 32 which receive self-tapping screws 33. The self-tapping screws 33 are utilized to fasten together the two U-shaped parts 13 and 14 with the U-shaped part 14 fitting over the top of the U-shaped part 13 with the front and rear walls 17 and 18 being received by the slots 28.

A spring clasp 36 of a conventional construction is secured to the bottom wall 16 by suitable means such as self tapping screws 37 secured to one of the members 38 and 39 forming a part of the clasp 36. The members 38 and 39 are hinged by a pivot pin 41. A spring 42 carried by the pivot pin 41 urges the distal extremities of the members 38 and 39 into engagement with each other as shown in FIG. 1. A handle 43 is secured to the top wall 21 of the case 12 and consists of a ring 44 which is carried by a U-shaped clamp 46 secured to the top wall 21 by a self tapping screw 47.

The clasp 36 and the handle 43 also can be formed of a suitable material such as metal.

A combination oscillator cartridge and needle valve assembly 51 is carried by the case and is mounted in the front wall 17. It consists of a body 52 having an inlet 53 and an outlet 54 with a flow passage 56 (see FIG. 6) extending between the inlet 53 and the outlet 54. A valve member 57 is carried by the body 52 and is movable between open and closed positions with respect to the outlet 54 and to thereby prevent the flow of gas through the flow passage 56 when the valve member 57 is in the closed position. A diaphragm 58 is also carried by the body 52 and is connected to the valve member 57 for causing movement of the valve member between its open and closed positions. The body 52 provides a chamber 59 on one side of the diaphragm 58 which is in communication with a servo port 61 carried by the body. A needle valve assembly 62 is carried by the body 52 and is provided with an adjustable flow orifice 63 which is connected between the inlet 64 and outlet 66.

The outlet 66 is connected to the servo port 61 of the oscillator cartridge body 52. The needle valve assembly 62 is provided with a knob 67 which is accessible from the front side of the front wall 17 for adjusting the orifice 63.

Three fittings 71, 73 and 74 are provided on the upper extremity of the rear wall 18 of the case 12 and are aligned in a row, with fitting 71 being the power fitting, fitting 73 being the nebulizer fitting and fitting 74 being the fitting for the combination venturi and exhalation valve assembly (phasitron) hereinafter described. First and second push button assemblies 76 and 77 are mounted on the front wall 17 near the lower extremity thereof and are each provided with push buttons 78 and 79 respectively. The push button assembly 76 serves as an inspiratory hold push button assembly and is provided with an inlet 81 and an outlet 82. The push button assembly 77 serves as an expiratory hold push button and is provided with an inlet 83 and an outlet 84.

An aerosol interruptor assembly 86 is provided in the case 12 and is mounted on the fitting 73 and has a normally closed position so as to prevent the escape of gas through the fitting 73. The interruptor assembly 86 is provided with an inlet 87 and an outlet 88. The details of this aerosol interruptor assembly will be described in conjunction with a subsequent embodiment of the present invention. It is provided to conserve gas when there is a necessity to do so in connection with an emergency situation.

The ventilator 11 also includes a nebulizer 91 and a combination venturi and exhalation valve assembly 92. The nebulizer 91 can be of the type described in U.S. application Ser. No. 671,491 filed Nov. 14, 1984. Similarly, the combination venturi and exhalation valve assembly 92 can be of the type described in co-pending application Ser. No. 516,133 filed July 21, 1983.

Figure 5:
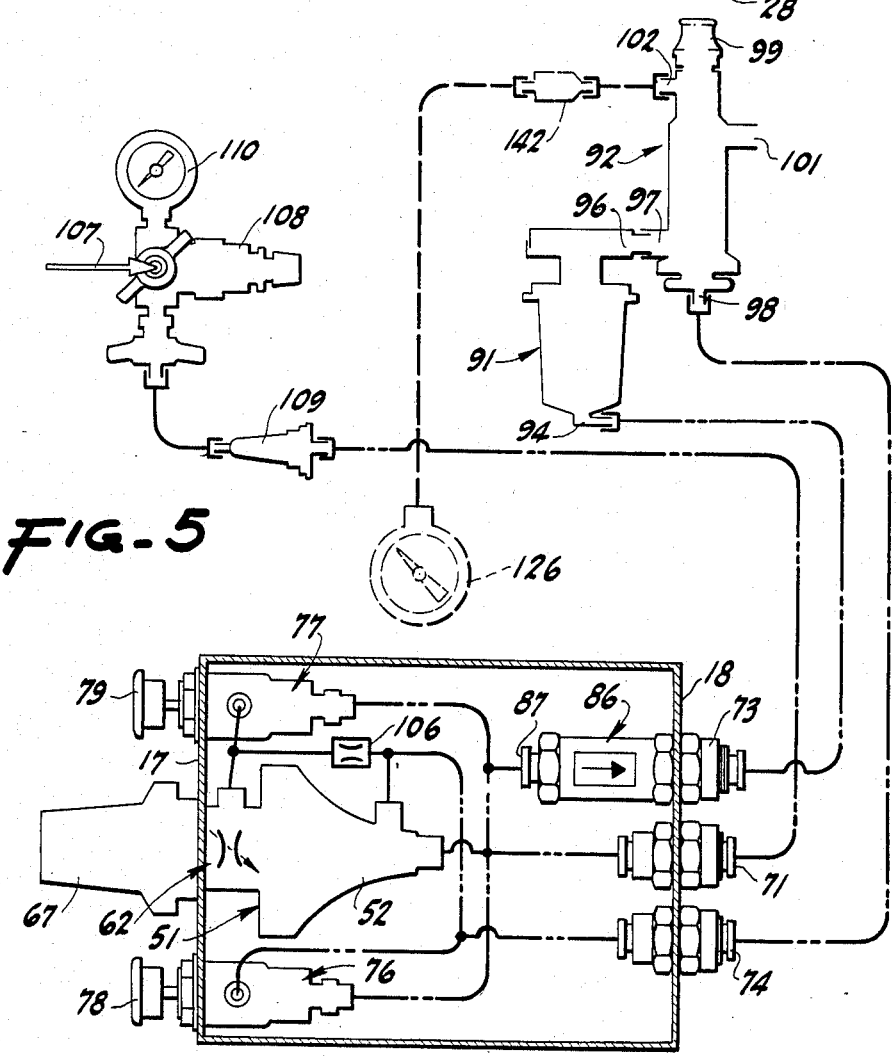
FIG. 5 is a physical schematic of the ventilator of the present invention.

The nebulizer 91 is provided with an inlet 94 and an outlet 96 (see FIG. 5). The outlet 96 is connected to an inlet 97 of the combination venturi and exhalation valve assembly 92. Certain of the details of the combination venturi and exhalation valve assembly 92 are described in co-pending application Ser. No. 866,790 filed May 23, 1986, now abandoned in favor of Ser. No. 111,139, filed Oct. 19, 1987, filed. As shown in FIG. 5, the combination venturi and exhalation valve assembly 92 includes an inlet 98 for the jet nozzle and an outlet 99 in the form of a patient adapter. It is also provided with an exhalation port 101 and a proximal airway sensing port 102 which can be capped when not used. The inlet 64 of the needle valve assembly 62 is connected through a balance orifice 103 to a junction 104. The junction 104 is connected through a loading orifice 106 to the fitting 74. The orifices 103 and 106 can be of a suitable size such as 0.013 and 0.060 inches respectively.

The ventilator 11 is adapted to be connected to a suitable pressurized gas source 107 through a pressure reduction regulator 108 and through a filter 109 to the power fitting 71. The pressure of the source gas after passing through the regulator 108 is measured by an operating pressure gauge 110.

Figure 6:
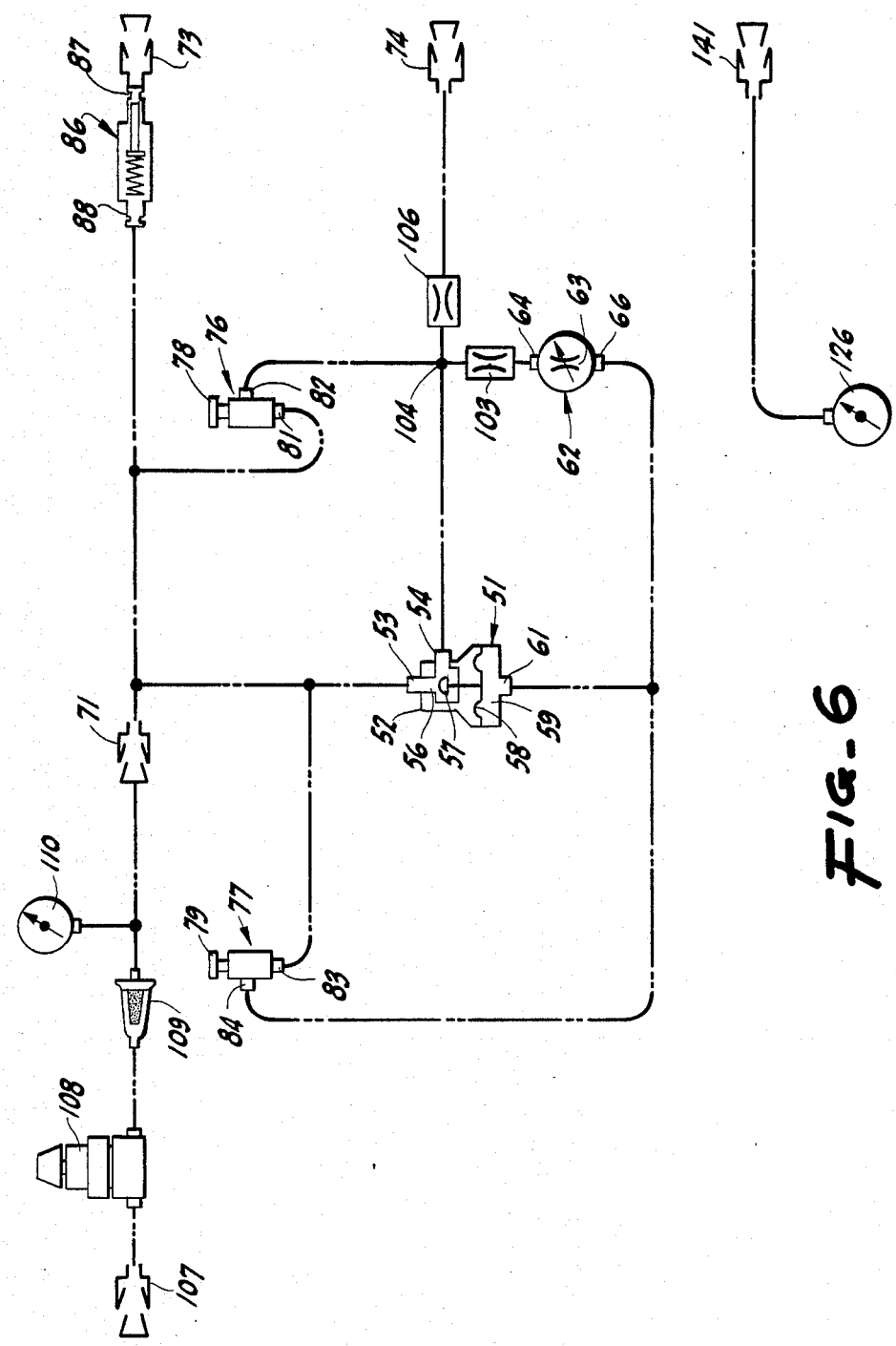
FIG. 6 is a pneumatic circuit diagram for the ventilator shown in FIGS. 1-5.

The operation and use of the ventilator shown in FIGS. 1-5 will be described hereinafter in conjunction with FIG. 6 and in connection with the additional embodiment which is disclosed in FIGS. 7-13.

Another embodiment of the ventilator 111 incorporating the present invention is shown in FIGS. 7-13. As shown therein, the ventilator 111 consists of a cylindrical case 112. The case 112 consists of a cylindrical central body 113 which has separable cylindrical end parts 114 and 116 secured thereto on opposite ends thereof. The central body 113 as well as the end parts 114 and 116 can be formed of a suitable material such as a transparent plastic. Cooperative mating means is carried by the ends parts 114 and 116 and the central body 113. This cooperative mating means can take the form of mating internal annular recesses 117 provided on opposite end of tee central body 113 and mating external annular recesses 118 provided on one end of each of the end parts 114 and 116. The recesses 117 and 118 are of such a size so that the parts 114 and 116 can be readily mated with the central body 113 to form a friction tight fit.

Circular ends plates 121 and 122 are mounted in the central body 113 and are adapted to seat in the internal annular recesses 117 provided on opposite ends of the central body 113. A combination oscillator cartridge and needle valve assembly 51 of the type hereinbefore described is mounted on the end plate 121 and is provided with a control knob 67 which is accessible from the open end of the end piece 114. A pressure gauge 126 is mounted on the other end plate 122 and is disposed in the end piece 116 so that the face of the pressure gauge 126 is visible from the open end of the end piece 116.

The fittings 71, 73, 74 and 141 provided in the previous embodiment of the ventilator 11 are also provided on the central body 113 with the fittings 71, 73 and 74 being aligned longitudinally of the central body 113 and with the fittings 71 and 141 being offset radially with respect to the fittings 73 and 74. A loading orifice 106 and a timing check valve 79 are also provided within the case 112.

Explosive decompression means is carried by the case 112 and consists of a pair of fittings 131 and 132 which are mounted in the central body 113 of the case 112 and vent the interior of the case 112 to atmosphere. In addition to the fittings 131 and 132, additional explosive decompression means carried by the case takes the form of the friction-tight fits which are formed between the end pieces 114 and 116 and the central body 113. In the event of an explosive decompression, the pressure of the gas within the central body 113 between the end plates 121 and 122 will push either one or both of the end plates 121 and 122 outwardly against the end parts 114 and 116 sufficient distance so that the end parts are separated from the central body and permitting gas to escape around the back sides of the end plate 121 and 122 to atmosphere.

In order to ensure that the end parts 114 and 116 will not accidentally fall off of the central body 114, resilient rubber rings 136 and 137 are provided which slip over the ends of the end parts 114 and 116 and are adapted to overlie the friction joint between the end parts 114 and 116 and the central body 113 to provide additional friction for retaining the end parts 114 and 116 on the central body 113. The rings 136 and 137 are provided with annular raised portions 139 adjacent the side edges of the same which frictionally engage the associated end part and the central body as shown particularly in FIG. 7. These rings 136 and 137 ensure that the end pieces 114 and 116 will not accidentally fall off of the central body 113 and also ensure that significant explosive decompression occurs prior to the end parts 114 and 116 separating from the central body 113.

The gauge 126 is connected through an orifice 141 to a pressure monitoring port 142 carried by the combination venturi and exhalation valve assembly 82.

Figure 13:
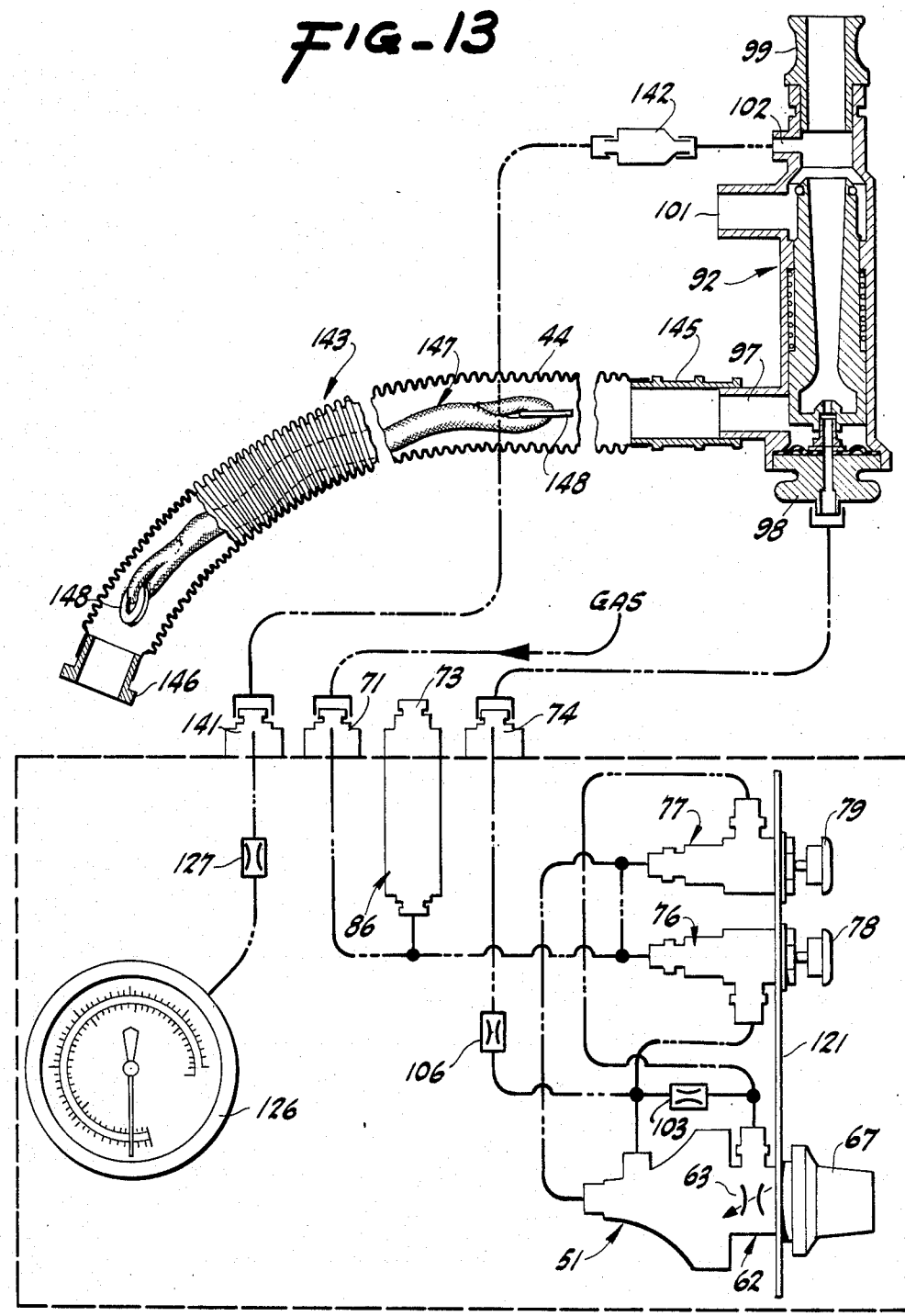
FIG. 13 is a physical schematic of the ventilator shown in FIGS. 7-12.

The power socket 71 of the ventilator 111 is connected to a suitable source of gas under pressure, as for example, in the manner shown in FIG. 5. The gas which is supplied to the power socket 71 is regulated as to pressure and is filtered. To make the ventilator particularly adapted for field applications as, for example, emergency or military situations in which it is desired to conserve source gas as much as possible, the nebulizer 91 (see FIG. 5) is removed. As shown in FIG. 13 there is substituted therefor an elongate tubular assembly 143 having which is formed of elongate flexible corrugated tubing 144 having end fittings 145 and 146. The end fitting 145 is mounted on the inlet 97 of the combination venturi assembly valve 92. The fitting 146 is provided with a passage which is in communication with the passage in the interior of the flexible tube 144. An elongate wick-like assembly 147 formed of a suitable material such as woven cotton is disposed within the tube 144. Washers 148 f a suitable material such as metal or plastic are fastened to the ends of the wick 147 and serve as weights to facilitate positioning the wick 147 within the interior of the tube 144. The wick 147 is sized in such a manner so that it can be introduced through either of the fittings 146 and 145. In order to introduce moisture into the air which is being drawn through the tube 144 as hereinafter described, the wick 147 is wetted with water in a suitable manner such as by dipping the wick into a body of water. The wick while still laden with water is then introduced into the tube 144 in such a manner so that it extends longitudinally throughout a substantial length of the tube 144.

The details of the aerosol interruptor assembly 86 hereinbefore identified is shown more particularly in FIG. 8. As shown therein, it consists of a body 151 formed of a suitable material such as plastic. The body 151 is cylindrical and is provided with a threaded boss 152 of reduced diameter which extends through the central body 113 and is secured thereto by nuts 153 threaded onto the boss 152 on opposite sides of the central body 113. The body 151 is provided with a central bore 154 which extends therethrough and is provided with a valve seat 156 which surrounds the bore 154. A plunger 157 is slidably mounted in the body 151 and extends through the bore 154. The plunger 157 is provided with a head 158 which carries an 0-ring 159 that is adapted to engage the valve seat 156. Means is provided for yieldably urging the plunger into engagement with the valve seat 156 to form an air-tight seal and consists of a spring 161 disposed in the bore 154 and which is retained therein by a threaded cap 162 which has the inlet 87 mounted therein. The cap 162 is provided with a bore 163 which is in communication with the bore 154 provided in the body 151. From the construction described it can be seen that the aerosol interruptor assembly 86 is in a normally closed position. It is adapted to be moved to an open position against the force of the spring 161 by a fitting 166. The fitting 166 is of the type described in co-pending application Serial No. 671,-491, filed November 14, 1984 so that when the fitting 66 is mounted thereon, the plunger 157 is moved to an open position and when the fitting 166 is removed, the aerosol interruptor assembly 86 returns to its normally closed position to prevent the escape of gas through the fitting 73.

As explained in co-pending application Serial No. 866,790 filed May 23, 1986, now abandoned in favor of Ser. No. 111,139, filed Oct. 19, 1987, filed, the ports 131 and 132 can be utilized to accommodate a pressure relief in the event of an explosive decompression. However, the fittings 131 and 132 have an alternative use as shown in FIG. 10 in which a length of flexible tube 167 of a suitable material such as plastic can be provided which has fittings 166 provided at opposite ends thereof which are adapted to snap on to the fittings 131 and 132. When this is the case, the tube 167 can be utilized as a loop or a strap to be placed about the neck of a patient so that the ventilator can be readily carried by the patient and be ambulatory with the patient.

In order to enhance the portability of the ventilator when used with a nebulizer, the combination venturi and exhalation valve assembly 92 and the nebulizer 91 secured thereto can be provided with means such as a clasp 171 of the type hereinbefore described which is secured to the combination venturi and exhalation valve assembly 92 and in a suitable manner such as by securing the same to the unused push button assembly 172 forming a part of the nebulizer 91. The clasp 171 is of a type which can be secured to the belt of the patient who is carrying the canister shown in FIG. 10.

Operation and use of the ventilators hereinbefore described can now be described in conjunction with the pneumatic circuit diagram shown in FIG. 6. Gas is supplied from the source 107 from a pressure of 10 pounds to 80 pounds to the source pressure regulator 108 which delivers gas of the desired pressure through a filter 109 to the operating pressure gauge 110 and also to the power fitting 71. Gas is supplied from the power fitting 71 to the inlet 53 of the normally open oscillator cartridge 51 which delivers the gas to the outlet 54 through the loading orifice 106 to the fitting 74 to the inlet 98 for the jet nozzle of the combination venturi and exhalation valve assembly 92 to deliver gas to the outlet 99 and into the airway and the lungs of the patient. Gas is also supplied to the needle valve assembly 62 through the balance orifice 103 which is adjustable to vary the inspiratory expiratory ratio as hereinafter described. Gas flows through the metering valve into the servo port 61 to apply gas under pressure to the diaphragm 58.

As soon as the pressure on the diaphragm is built up sufficiently, the valve member 57 of the normally open cartridge is moved to a closed position to occlude the flow passage through the inlet and outlet 54 to interrupt the flow of gas to the combination venturi and exhalation valve assembly 92. As soon as the flow of gas has been interrupted through the outlet 54, the gas under pressure behind the diaphragm 58 begins unloading through the same metering valve 62 and then through the combination venturi and exhalation valve assembly 92. As soon as sufficient unloading has occurred, the oscillator cartridge 51 will move to its normally open position to again permit gas to flow from the inlet to the outlet and into the lungs of the patient to again start operation of the timing circuit for closing the oscillator cartridge 51.

From the foregoing it can be seen that the length of the inspiratory and expiratory phases can be controlled by the use of the single metering valve 62. When the metering valve 62 is completely open, the inspiratory and expiratory times should be approximately equal giving a one-to-one IE ratio. As the metering valve 62 is closed down, the expiratory time is lengthened and the inspiratory time is decreased. By properly controlling the metering valve 62, it is possible to control the expiratory phase so that there is no stacking of breaths by the patient. In other words, there is ample opportunity by providing longer expiratory phases to permit the patient to completely expel the air from the lungs before an inspiratory phase is commenced.

The loading orifice 106 determines how rapidly the lungs of the patient will be loaded up. It is utilized to make the operation of the metering needle valve 62 less critical.

In addition, two manual valves, the inspiratory hold and expiratory hold push button valves, 76 and 77 are provided. It can be seen for example that the inspiratory hold push button assembly 76 makes it possible by manually depressing the push button 78 to place the ventilator on an inspiratory hold by delivering the source gas from the regulator 108 directly through the loading orifice 106 into the combination venturi jet and exhalation valve assembly 92. Operation of the inspiratory hold push button assembly 76 supplies gas through the metering valve 62 to the oscillator cartridge 51 so that it is loaded to move the normally open cartridge to its closed position. This ensures that when the inspiratory hold push button 70 is released that the ventilator will always start from an expiratory phase.

As explained previously, an expiratory hold push button assembly 77 is provided which takes source gas from the regulator and supplies it directly to the timing circuit to load the diaphragm 58 of the normally open cartridge to move it to the closed position and to retain it in that position as long as the expiratory hold push button 79 is manually depressed.

It can be seen from the foregoing that there has been provided a very simple regulator which makes possible diffusive convective type ventilation with high frequency pulses. It is relatively small and compact so that it can be utilized as a transporter ventilator for use in emergency and trauma situations. It can be utilized either to assist or control the spontaneous breathing of the patient. The use of the combination venturi and exhalation valve assembly 92 makes it possible for the patient to breathe at a commanding rate chosen by him if he so desires. This pneumatic clutching feature provided by the combination venturi and exhalation valve assembly 92 makes the ventilator very safe to operate without any danger of injuring a patient.

The ventilator is also very economical in its use of gas. For example, 600 liters of gas can be utilized to operate the ventilator for a period of up to four hours. With the arrangement shown in FIG. 6, it is possible with a single valve 62 to allow cyclic operation as rapid as 300 to 400 times a minute at a one-to-one IE ratio down to approximately four times a minute with an IE ratio of one-to-five or one-to-six. The ventilator is particularly adapted for transport to remote locations with a small bottle of source gas. When it is particularly desirable to conserve gas, the nebulizer 91 need not be operated. When this is the case, the fitting 166 is removed from the socket 73 which permits the aerosol interruptor cartridge 86 to move to a normally closed position to prevent the escape of the gas through the socket or fitting 73.

This ensures that the ventilator would utilize a minimum amount of gas. Humidification of gasses can still be provided by using a hose assembly 143 shown in FIG. 13 in which the wick has been soaked with water. Air passing over the wick 147 will pick up water from the wick and thus will be humidified.

In the first embodiment of the invention, a pressure gauge was not utilized to make possible a smaller case. In the second embodiment a pressure gauge has been provided for measuring the proximal airway pressure. Even this unit which is provided with a pressure gauge is very compact and can be readily transported by use of the strip or lanyard 167 for the cylindrical canister-like case 112 and by the use of clasp 171 for the combination venturi and exhalation valve assembly 92 and nebulizer 91.

As explained in co-pending application Ser. No. 866,790 filed May 23, 1986, now abandoned in favor of Ser. No. 111,139, filed Oct. 19, 1987, filed, there is provided means for accommodating explosive decompression in both embodiments of the ventilator.

Thus it can be seen that the ventilators of the present invention can be utilized without any humidifier or if humidification is desired, a nebulizer 91 of the type shown in FIGS. 11 and 12 can be utilized or alternatively, a humidifier tube assembly 143 can be utilized in place of the nebulizers 91 to provide the humidification desired for the gasses being supplied to the pulmonary structure of the patient.

Figure 14:
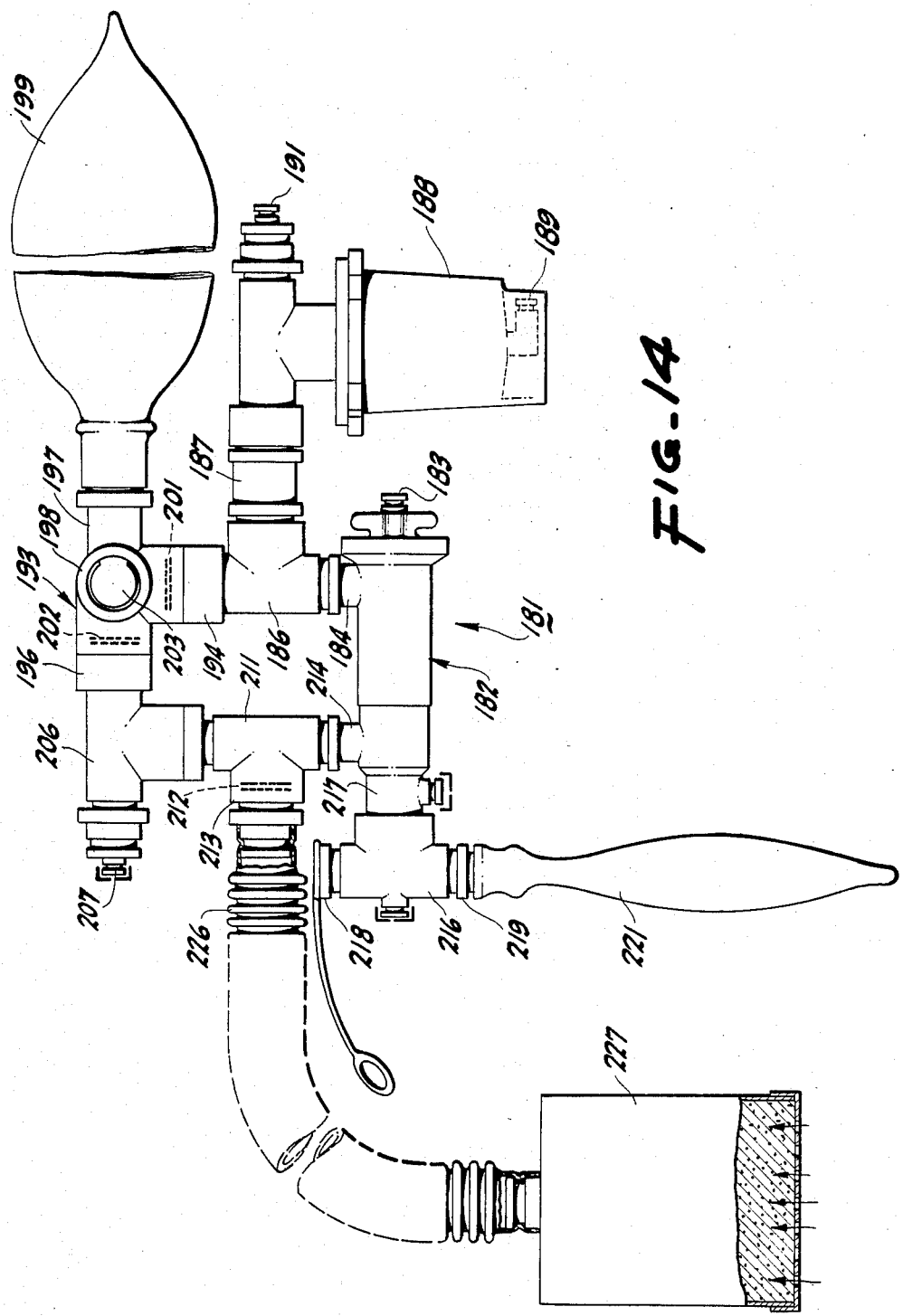
FIG. 14 is a plan view of a breathing circuit for a ventilator incorporating the present invention which can be used in military applications

The ventilator of the present invention is particularly adapted for use in military applications because of its ease of transport and economical use of gas. In connection with such military applications, a breathing tube assembly 181 such as shown in FIG. 14 can be utilized. As shown therein, it consists of a combination venturi jet and exhalation valve assembly 182 which is provided with an inlet 183 that is supplied from the phasitron socket 74. It is provided with an inlet 184 which has a tee 186 mounted thereon that has an inspiratory fail-safe valve 187 mounted thereon. A nebulizer 188 of the type hereinbefore described is mounted on the inspiratory failsafe valve 187. It is provided with a gas fitting 189 as well as with a gas fitting 191 to supply nebulized gasses through the inspiratory check valve 187 and through the tee 186 into the combination venturi jet and exhalation valve assembly 182.

The other leg of the tee 186 is connected to a cross-type member 193 having a plurality of legs 194, 196, 197 and 198. The legs 194, 196 and 197 lie in a plane with the leg 198 extending at right angles thereto. The legs 194, 196, and 198 all have one-way valve members 201, 202 and 203 disposed therein. Another tee 206 is mounted in the leg 196 of the tee 193. One leg of the tee 206 is closed by a cap 207. The other leg is connected into another tee 211 which is provided with a one-way valve 212 mounted in a leg 213 of the tee 211. The tee 211 is connected to the exhalation port 214 of the combination venturi jet and exhalation valve assembly 182. A tee 216 is mounted on the outlet 217 of the combination venturi jet and exhalation valve assembly 182. One end of the tee 216 is capped by a cap 218. The other leg of the tee 216 serves as a patient adapter 219 and is connected to a rubber bag 221 representing the lungs of a patient.

An elongate flexible tube 226 of the type hereinbefore described is connected to the leg 213 of the tee 211 and, if desired, can be provided with a wick which can be wetted of the type hereinbefore described in conjunction with FIG. 13. The tube 226 is provided for entraining ambient air and, if desired, for providing humidified ambient air if it is not desired to utilize the nebulizer 188. In order to make the ventilator using a breathing circuit such as that shown in FIG. 14 for use in biological and chemical warfare, the breathing tube 226 can be connected to a canister 227. The canister 227 can be a canister which has been adapted to make it possible for the wearer to operate where biological warfare is taking place. By way of example, the canister 227 could contain ingredients to neutralize certain gasses such as, for example, mustard gas. The canister also can be designed to make it possible to neutralize other gasses. Canisters of such a type are well known to those skilled in the art and thus will not be described in detail.

The breathing circuit shown in FIG. 14 provides great flexibility. The circuit can be utilized as a closed breathing circuit in which certain of the gasses exhausted by the patient will be collected by the bag 199 and then reintroduced into the patient as required by the patient. In the event that additional gasses are needed for ambient, those gasses can be drawn into the breathing circuit through the canister 227 and past the one-way check valve 212. The valve 203 serves to exhaust gasses expelled by the patient's lungs to the atmosphere, particularly that which is in excess of that which can be retained by the bag 199. Since the valve 203 is a one-way valve gasses cannot be entrained from the atmosphere and if such gasses are desired by the patient they must be drawn in through the canister 227. This ensures that the patient can exist in a biological warfare zone without the necessity of breathing such gasses without them passing through the canister 227. The breathing circuit is one in which nebulized gasses can be introduced by the use of a nebulizer. In the event it is desirable to conserve gas, a wettened wick placed in the tube 226 can be substituted for the nebulizer.

It should be appreciated that the bag 199 can also be utilized for supplying air to the airways of the patient by the manipulation of the bag 199.

It is apparent from the foregoing that there has been provided a ventilator which can be readily transported from one location to another and can be utilized in many different types of situations including medical and military applications.

What is claimed is:

1. In a ventilator adapted to be connected to a source of gas under pressure, a case, an inlet adapted to be connected to the source of gas, an oscillator cartridge carried by the case and having a body, the body having an inlet and an outlet and a flow passage interconnecting the inlet and an outlet, a valve member carried by the body and movable between open and closed positions with respect to the outlet, diaphragm means carried by the body and connected to the valve member for moving the valve member between open and closed positions to interrupt the flow of gas in the flow passage between the inlet and the outlet, servo port means carried by the body for supplying gas to the diaphragm for causing movement of the diaphragm to thereby cause movement of the valve member to the closed position to interrupt the flow of gas in the flow passage between the inlet and the outlet, adjustable metering valve means for metering the flow of gas from the outlet to the servo port to provide for cyclic operation of the oscillator cartridge between inspiratory and expiratory phases, a patient adapter having an inlet and an outlet, pneumatic clutching means having an inlet and an outlet coupled to the inlet of the patient adapter, means coupling the outlet of the oscillator cartridge to the inlet of the pneumatic clutching means, said adjustable metering valve means having a single control knob whereby adjustment of the single control knob changes the frequency of cyclic operation and the ratio between the inspiratory phase and the expiratory phase.

2. A ventilator as in claim 1 together with a loading orifice connected between the outlet of the oscillator cartridge and the inlet to the pneumatic clutching means.

3. A ventilator as in claim 2 together with manually operated inspiratory push button means for supplying gas directly to the adjustable metering valve means through the loading orifice and to the outlet of the oscillator cartridge for supplying inspiratory gasses through the loading orifice to the airway of the patient and through the adjustable metering valve means for loading the diaphragm of the oscillator cartridge.

4. A ventilator as in claim 3 together with manually operated expiratory hold push button means supplying gas directly to the servo port.

5. A ventilator as in claim 3 together with mandated means for loading the ventilator into the expiratory phase when the ventilator is placed in operation to prevent supplying to a patient a double inspiratory phase.

6. A ventilator as in claim I together with a nebulizer having input and output, means connecting the source to the input of the nebulizer, means connecting the output of the nebulizer to the pneumatic clutching means and interrupting means for interrupting the source of gas to the nebulizer.

7. A ventilator as in claim 6 wherein said interrupting means is comprised of a body having a flow passage therein, a valve seat encircling the flow passage, a plunger movable in the flow passage and carrying a valve member adapted to move into sealing engagement with the valve seat and spring means carried in the body for yieldably urging the plunger toward a normally closed position in which the valve member engages the valve seat.

8. A ventilator as in claim 1, together with explosive decompression means carried by the case.

9. A ventilator as in claim 1 together with means for supplying moisture to the patient adapter.

10. A ventilator as in claim 9 wherein said means for supplying moisture to the patient adapter includes an elongate tube and a moisture carrying wick disposed in the elongate tube whereby at least certain of the gasses supplied to the patient adapter pass through the flexible elongate tube and pick up moisture from the moisture carrying wick in the tube.

11. A ventilator as in claim 1 together with one-way valve assembly coupled to the patient adapter, and a gas canister coupled to the one-way valve assembly so that additional air entrained by the patient must pass through the gas canister.

12. A ventilator as in claim 11 together with a combination venturi jet and exhalation valve assembly connected to the one-way valve assembly and means for supplying gas to the combination venturi jet and exhalation valve assembly.

13. A ventilator as in claim 12 together with an additional one-way valve assembly couple to the combination venturi jet and exhalation valve assembly and flexible bag means connected to the additional one-way valve assembly for collecting at least certain of the gasses exhaled by the patient so that they can be reintroduced into the lungs of the patient.

14. A ventilator as in claim 1 together with a mandated means for exponentially increasing expiratory time as inspiratory time and associated intrapulmonary tidal volumes are increased.

* * * * *